United States Patent [19]

Dimarco

[11] Patent Number: 5,499,986
[45] Date of Patent: Mar. 19, 1996

[54] QUICK RELEASE HANDLE APPARATUS FOR REMOVING AND INSERTING INTRAMEDULLARY NAILS

[75] Inventor: Donna M. Dimarco, Memphis, Tenn.

[73] Assignee: Smith & Nephew Richards Inc., Memphis, Tenn.

[21] Appl. No.: 178,771

[22] Filed: Jan. 7, 1994

[51] Int. Cl.$^6$ .......................................... A61F 5/00
[52] U.S. Cl. ............................................ 606/104; 606/99
[58] Field of Search ................ 606/104, 86, 96–104; 81/177.85; 403/321, 322, 325, 326; 279/75, 905

[56] References Cited

U.S. PATENT DOCUMENTS

| | | | |
|---|---|---|---|
| 4,169,470 | 10/1979 | Ender et al. | 128/92 |
| 4,306,550 | 12/1981 | Forte | 128/92 |
| 4,583,270 | 4/1986 | Kenna | 29/80 |
| 4,587,964 | 5/1986 | Walker et al. | 128/92 |
| 4,601,289 | 7/1986 | Chiarizzio et al. | 128/305 |
| 4,765,328 | 8/1988 | Keller et al. | 128/303 |
| 4,921,493 | 5/1990 | Webb, Jr. et al. | 606/85 |
| 4,990,149 | 2/1991 | Fallin | 606/85 |
| 5,013,194 | 5/1991 | Wienhold | 279/75 |
| 5,028,181 | 7/1991 | Jenkins | 279/75 |
| 5,089,003 | 2/1992 | Fallin et al. | 606/85 |
| 5,089,004 | 2/1992 | Averill et al. | 606/85 |
| 5,178,621 | 1/1993 | Cook et al. | 606/96 |
| 5,190,549 | 3/1993 | Miller et al. | 606/85 |
| 5,190,550 | 3/1993 | Miller et al. | 606/85 |
| 5,308,350 | 5/1994 | Mikhail | 606/86 |

FOREIGN PATENT DOCUMENTS

| | | |
|---|---|---|
| 0504521A1 | 9/1992 | European Pat. Off. . |
| 2627983 | 9/1989 | France .................. 606/99 |

*Primary Examiner*—Robert A. Hafer
*Assistant Examiner*—David J. Kenealy
*Attorney, Agent, or Firm*—Pravel, Hewitt, Kimball & Krieger

[57] ABSTRACT

A quick release handle apparatus for pulling an intramedullary nail includes a handle body with a sliding pushrod that moves an outer cylindrical member over an inner cylindrical member having locking elements. The locking elements engage an annular groove on a nail puller element that attaches to an intramedullary nail. The outer cylinder overlaps the inner cylinder at the locking balls to define the locking position.

25 Claims, 8 Drawing Sheets

QUICK RELEASE HANDLE APPARATUS FOR REMOVING AND INSERTING INTRAMEDULLARY NAILS

BACKGROUND OF THE INVENTION

1. Field of the Invention

The present invention relates to surgical instruments and more particularly to an improved orthopedic surgical instrument that is used to remove or insert an elongated intramedullary rod from the intramedullary canal of a patient's bone. More particularly the present invention relates to an improved quick release handle that forms a quick release connection with the top of an intramedullary rod that has been surgically implanted. Even more particularly the present invention relates to an improved quick release handle and an accompanying separate nail puller element that threadably attaches to the top of the intramedullary rod. At its opposite end the nail puller element releasably attaches to the distal end portion of the handle. Quick connect and quick disconnect with the nail puller is achieved using a plurality of circumferentially spaced ball bearings on the handle that engage an annular groove on the nail puller.

2. General Background

Elongated intramedullary rods are commonly used to repair bone fractures of a patient's long bone (eg. femur). These intramedullary rods are often used in combination with bone screws. For example, U.S. Pat. No. 5,167,663 issued to Brumfield describes an intramedullary rod having diagonal extending openings at its proximal end portion and transversely extending openings at its distal end portion. In the Brumfield patent the diagonal openings are directed towards the patient's acetabulum. Transverse are provided at the distal end of the rod, to be occupied by transverse bone screws. U.S. Pat. No. 5,167,663 is hereby incorporated herein for reference.

Intramedullary nails have been removed with instruments that can removably attach to the proximal end of the nail. An example of such a nail and a tool for removing that nail is seen in U.S. Pat. No. 4,169,470 entitled "Surgical Nail for Use in Setting Bone Fractures, and Tool for Emplacing Same" issued to Josef Ender and Hans G. Ender. The Ender patent shows an intramedullary nail having a specially shaped end portion that excepts a tool. The tool resembles a pair pliers having a nose portion that moves into a recess for gripping the nail so that the nail can be withdrawn or angularly adjusted when the connection is made between the tool and the nail. Other embodiments show other connections between the removal tool and the top of the nail.

Prior to the insertion of a femoral prothesis, a rasp tool is often used to shape the patient's intramedullary canal. It has been known in the art to manipulate these rasps using handles. These rasp handles have been equipped with a quick connect coupling to quickly connect/disconnect with the rasp. An example of such a rasp and handle assembly is shown U.S. Pat. No. 4,306,550 entitled "Combination Including Femoral Rasp and Calcar Facing Reamer", naming Mark Forte as inventor. The Forte patent discloses a combination of tools and methods used to prepare a socket in a femur for receiving a femoral prothesis including a rasp having a cutting portion and a pilot post portion, a handle assembly with a chuck for releasably engaging the pilot post portion to facilitate working the rasp into a femur, and a cutter device adapted to be journaled on the pilot post and power driven to surface the calcar adjacent the socket. After a socket is formed in the femur by use of a rasp and handle assembly, the rasp is left in the socket. The handle assembly is then removed, and the cutter is journaled over the pilot post and rotated by a drive apparatus.

The Kenna patent 4,583,270 entitled "Rasp Handle" discloses a rasp handle that has an elongated body portion with a pistol type grip extending therefrom and with a rasp retaining structure at its opposite. The structure includes a fixed jaw and a slide jaw constructed and arranged for sliding movement relative to the fixed jaw between a forward closed locking position where a rasp is locked between the jaws and a rearward open rasp receiving and releasing position. The lever is connected to shift the slide jaw between its open and closed positions. A pivot interconnects the lever and the slide jaw so that the lever is free to move between a locked position adjacent the body portion and an unlocked jaw manipulating position away from the body portion. Another rasp tool that includes a handle is disclosed in Walker's patent 4,587,964 entitled "Rasp Tool". The Walker patent includes a handle and a cutter as part of the rasp tool. The handle carries a releasable locking assembly to couple the cutter to the handle and the releasable locking assemble is compactly arranged at one end of the handle via transversely extending flange which also acts as spacer between the releasable locking assembly and the roughened outer surface of the cutter.

In the Chiarizzio patent 4,601,289 there is disclosed a femoral trial prothesis/rasp assembly used in hip implant surgery. The assembly includes a handle that grips the combination trial prothesis/rasp in a secure manner by clamping over and locking on to a post on the trial prothesis/rasp which later serves as a mounting piece for a femoral prothesis head used in trial reductions.

A coupling arrangement for selectably coupling and uncoupling a handle and the blade of a surgical instrument such as a broach is disclosed in the Keller patent 4,765,328.

The Webb patent 4,921,493 discloses a rasp tool that comprises a handle and a cutter. The rasp tool carries a releasable locking assembly to couple the cutter to the handle. The releasable locking assembly is compactly arranged at the distal end of the handle and the mating proximal end of the cutter. The assembly includes a first interconnecting means for opposing longitudinal separation between the handle and the cutter, and a second inter connecting means for opposing lateral motion between the cutter and the handle. The releasable locking assembly is set to manually control attaching and detaching the cutter to the handle.

A releasable orthopedic broach handle apparatus is the subject of U.S. Pat. No. 4,990,149 issued to Thomas W. Fallin and naming Richards Medical Company as assignee. The Fallin patent discloses a modular broach handle for use with a broach having a tapered configuration beginning at a wider upper end and tapering to a smaller lower end. An elongated handle body portion has a longitudinal axis, with one end portion of the handle body defining a connection end portion for attaching a broach thereto at the wider upper end portion of the broach. A slot extends a distance along the handle terminating at one end thereof adjacent a connection end portion with the handle body. A socket communicating with the slide is formed at the connection end portion of the handle body, the socket having an open end portion receptive of an attachment post on the wide end portion of the broach. A spring loaded slider bar is disposed within the slot for sliding movement therewith and with respect to the handle between engaged and disengaged positions, and includes an end portion that extends into the socket when in an engaged position to form a connection with the post. Slider bar and handle socket form a releasable locking mechanism between the post of the broach and the handle that is perfected upon assembly by pushing the post onto the socket, without manipulation of the slider bar.

U.S. Pat. No. 5,089,003 entitled "Rasp Tool Including Detachable Handle Member" discloses a rasp tool, handle member, and cutter member and a releasing locking mechanism for selectively coupling the handle and the cutter member. The locking mechanism includes a locking post on cutting member and a corresponding post receiving bore in the handle member. A spring-biased locking key is disposed within a guide bore that intersects the post receiving bore such that the locking key extends partially into the post receiving bore. As the locking post is actually introduced into the post receiving bore, the locking post contacts the locking key and causes it to retract until the locking post is fully received within the bore at which point the spring-biased locking key engages a transverse notch in the locking post thereby preventing actual removal of the post from the bore. The locking key is disengaged from the locking post by a trigger coupled to the locking key.

The Averill patent 5,089,004 provides a prosthetic implant procedure and femoral broach that includes a handle that forms a connection with the broach.

A locking surgical tool handle system is disclosed in U.S. Pat. No. 5,190,549, issued to Gary Miller and Matthew Lyons. The '549 patent discloses a surgical tool handle that has an elongated body portion with a pistol type grip. The front end of handle body has a tool retaining structure comprising a contoured engagement face and a moveable tension bar within an engagement end. Projections on the engagement end of the tension bar fit within a receiving channel of a surgical tool such as a broach or rasp. A locking mechanism is provided within the handle body and is implemented with pivotal links attached to the tension bar. The locking mechanism has an unlocked position in which the engagement end of the tension bar is spaced away from the engagement face of the handle body and an over center locked position which the engagement end of the tension bar is retracted toward the handle body. When the tool handle is placed in the locked position the engagement end of the tension bar pulls the attached tool into tight contact with the engagement face of the handle body.

SUMMARY OF THE PRESENT INVENTION

The present invention provides a quick release handle apparatus for inserting and/or pulling an intramedullary nail from the intramedullary canal of a patient's bone (eg. femur). The apparatus includes a handle body with proximal and distal end portions. The handle supports a trigger that is movably disposed relative to the handle between locking and releasing positions. The trigger operates a longitudinally extending pushrod. The proximal end of the handle body has a socket with a central axis.

A nail puller element forms a connection at its distal end portion with the intramedullary rod, preferably forming a threaded connection therewith. The intramedullary rod has an internal bore that extends longitudinally, substantially the length of the intramedullary rod. The upper end portion of the bore at the proximal end of the rod is internally threaded. The nail puller is preferably externally threaded so that the distal end of the nail puller threadably engages the proximal end of the intramedullary rod.

The nail puller has a proximal end portion that includes an annular groove for forming a connection with a plurality of locking balls circumferentially spaced about a socket at the distal end portion of the handle body. The trigger and pushrod are movably mounted on the handle body between "releasing" and "locking" positions.

In the "releasing" position, the locking balls are allowed to retract as the handle body forms a connection with the nail puller. This connection is made at an annular head portion of the nail puller. As the balls retract, an enlarged head portion of the nail puller passes the balls. In the "locking" position the trigger is released, and a spring urges the trigger and pushrod towards the distal end of the handle body. The pushrod is connected to a link that moves a cylindrical sleeve over the locking balls, forcing them inwardly towards the socket and into engagement with the annular groove portion of the nail puller adjacent the enlarged head, forming a rigid connection therewith as the balls prevent removal of the enlarged head when in locking position.

Once this connection is completed, a surgeon can remove or insert the intramedullary nail by hammering or otherwise applying force to the handle at an anvil on the proximal end of the handle.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
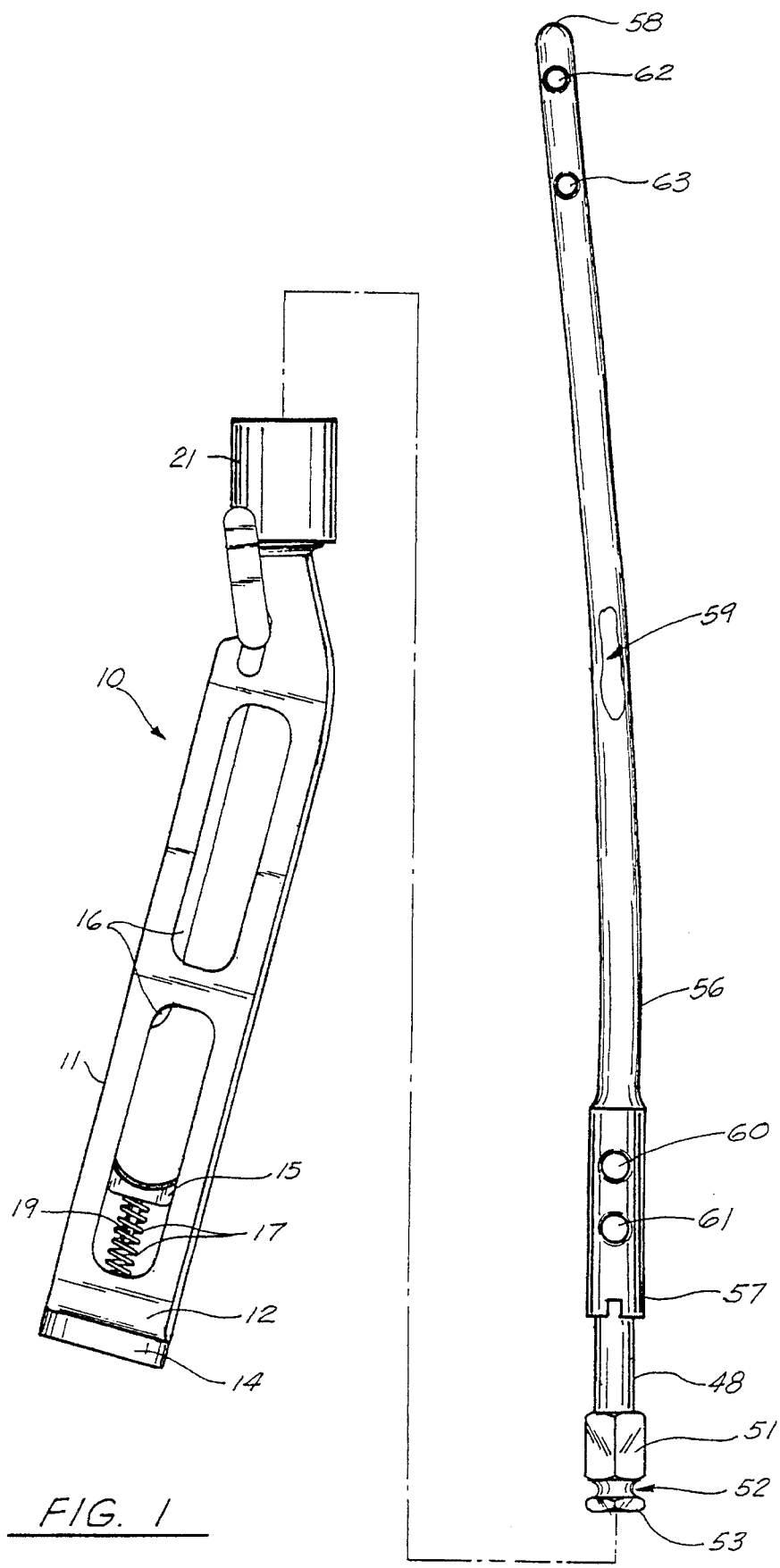
FIG. 1 is a side view of a first embodiment of the apparatus of the present invention.
Figure 2:
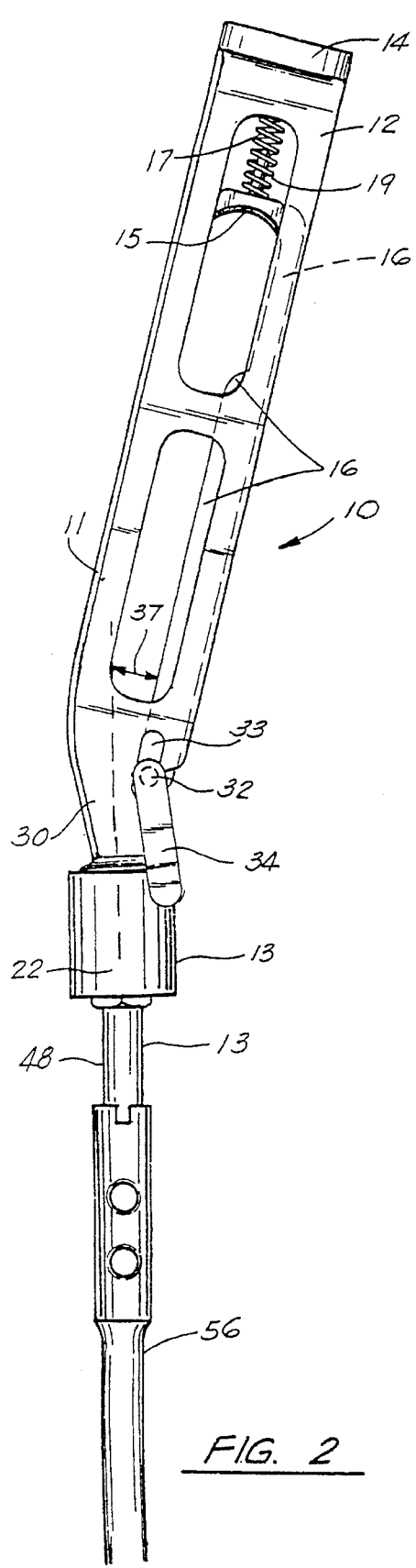
FIG. 2 is a side view of the first embodiment of the apparatus of the present invention shown in locking position.
Figure 3:
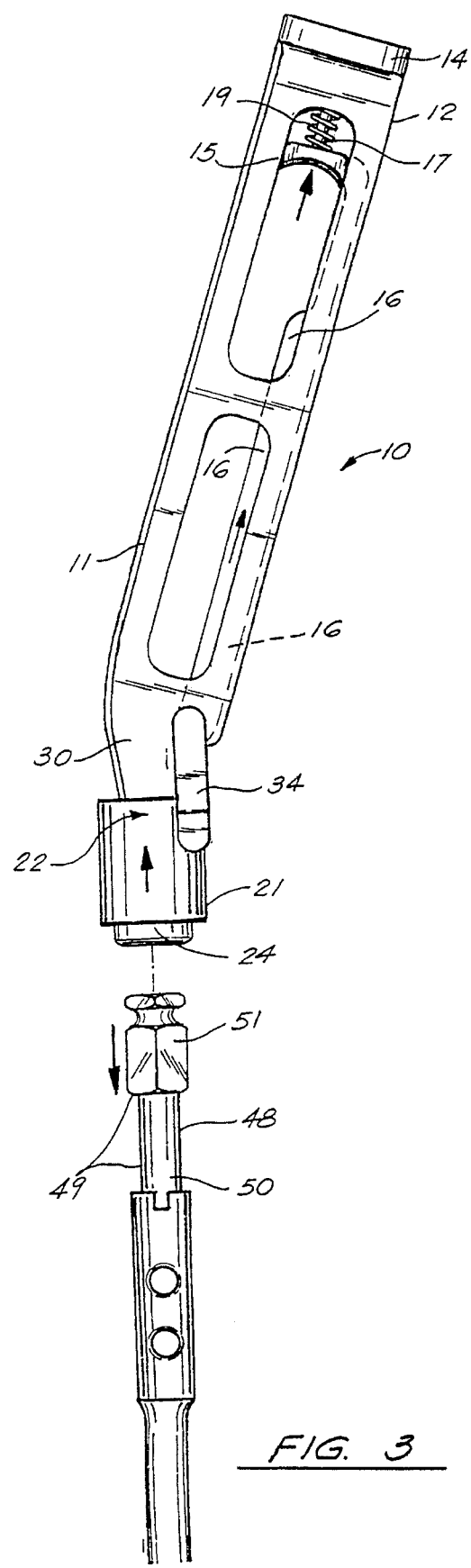
FIG. 3 is a side view of the first embodiment of the apparatus of the present invention with the nail puller in released position.

FIGS. 1–5 show generally a first embodiment of the apparatus of the present designated generally by the numeral 10. Medullary nail inserter and remover 10 includes a frame or body in the form of an elongated handle 11 having a proximal end 12 and a distal end 13. The proximal end 12 of the handle provides an anvil 14 that can be hammered or otherwise impacted by a user in order to insert or to remove the handle and an attached intramedullary rod 56. Placement of intramedullary rods per se in a patient's femur is discussed in U.S. Pat. No. 5,167,663 incorporated herein by reference.

A trigger 15 and pushrod 16 are preferably integral and moveable relative to the handle body 11. The trigger 15 moves between "releasing" and "locking" positions. When the surgeon pulls the trigger 15 towards anvil 14 and overcomes the spring 17 pressure, this defines the "releasing" position. When the surgeon releases the trigger, spring 17 urges trigger 15 and its pushrod 16 towards the distal end 13 of the handle body 11 to define the "locking" position. Trigger 15 and pushrod 16 can be an integral part.

Handle body 11 has a longitudinal slot 18 that is occupied by pushrod 16. Trigger 15 tracks slot 18 and a longitudinal groove 20 in handle 11. Post 19 extends from rear of trigger 15 and is surrounded by coil spring 17. Spring 17 is held in position by virtue of its placement on post 19. The coil spring 17 presses at one end portion against trigger 15. The opposing end portion coil spring 17 fits against handle 11 at opening 19A.

Figure 6:
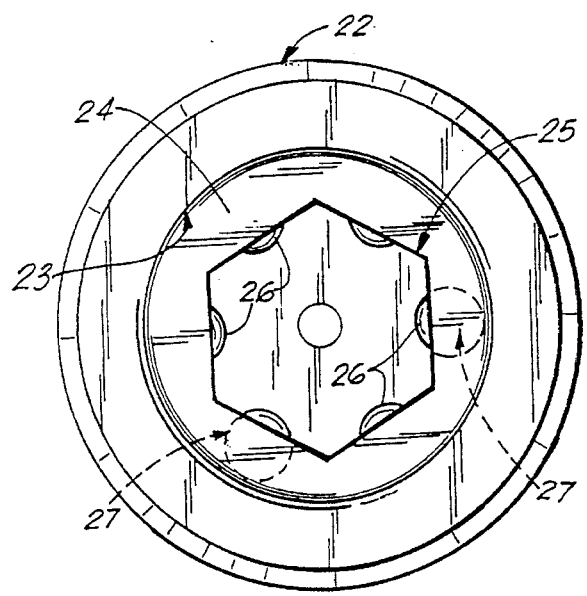
FIG. 6 is a fragmentary end view of the first embodiment of the apparatus of the present invention.
Figure 15:
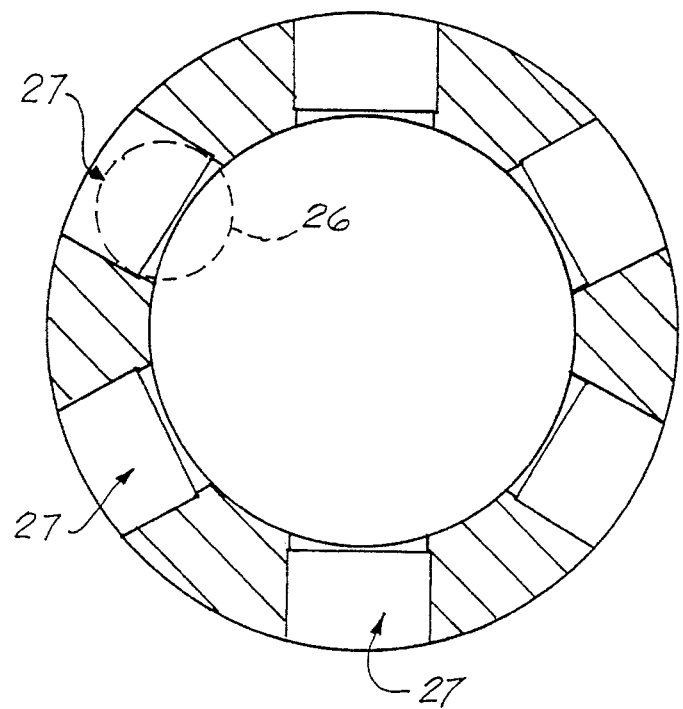
FIG. 15 is a fragmentary view of the second embodiment of the apparatus of the present invention.
Figure 16:
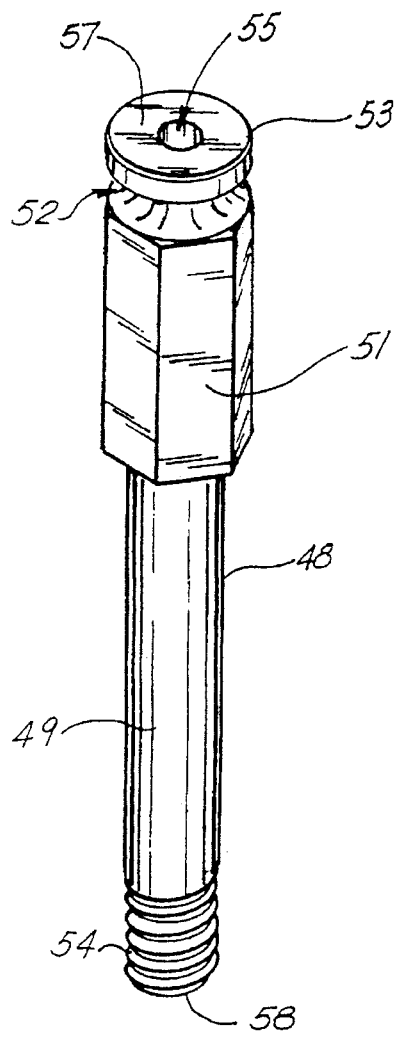
FIG. 16 is a fragmentary perspective view of another nail puller used with the first and second embodiments of the apparatus of the present invention.
Figure 17:
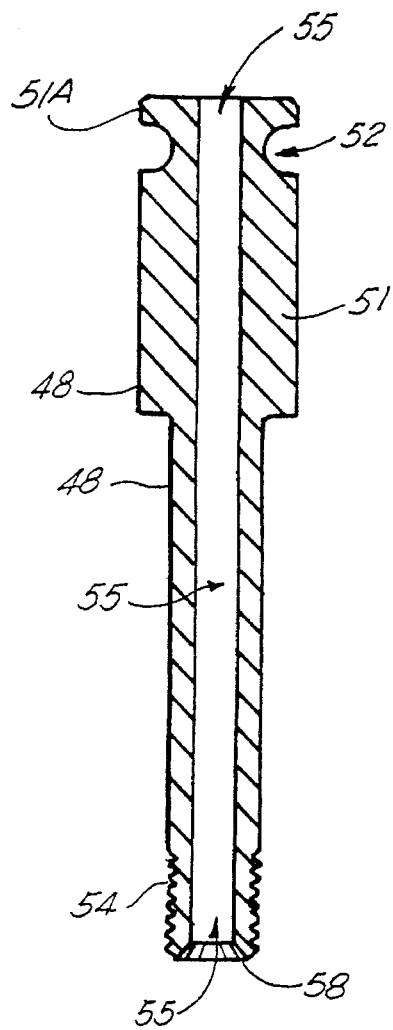
FIG. 17 is a sectional view of the nail puller of FIG. 16.

The distal end 13 portion of handle body 11 provides a cylindrical sleeve 21 having an outer surface 22 and an inner surface 23. Sleeve 21 surrounds cylindrically shaped member 24. Cylindrical member 24 provides an open socket that includes a hexagonal (see FIG. 6) or circular (see FIG. 15) portion 25. Socket portion 25 carries a plurality of locking balls 26. Each locking ball 26 is carried in an opening 27. The openings 27 are sized and shaped to allow each ball 26 to extend well into socket 25. However, the balls 26 do not fall into the socket 25. Each opening 27 is sized to allow almost one-half of a particular ball 26 to enter socket 26 (see FIGS. 6–8). A majority of each locking ball 26 is retained within opening 27 at all times.

Cylindrical member 24 includes an annular end portion 29 that has a beveled annular surface portion 28. Beveled annular surface 28 allows each of the locking balls 26 to retreat fully into opening 27 so that nail puller element 48 can be removed when the trigger 15 is pulled to the "releasing" position (see FIG. 8).

Figure 10:
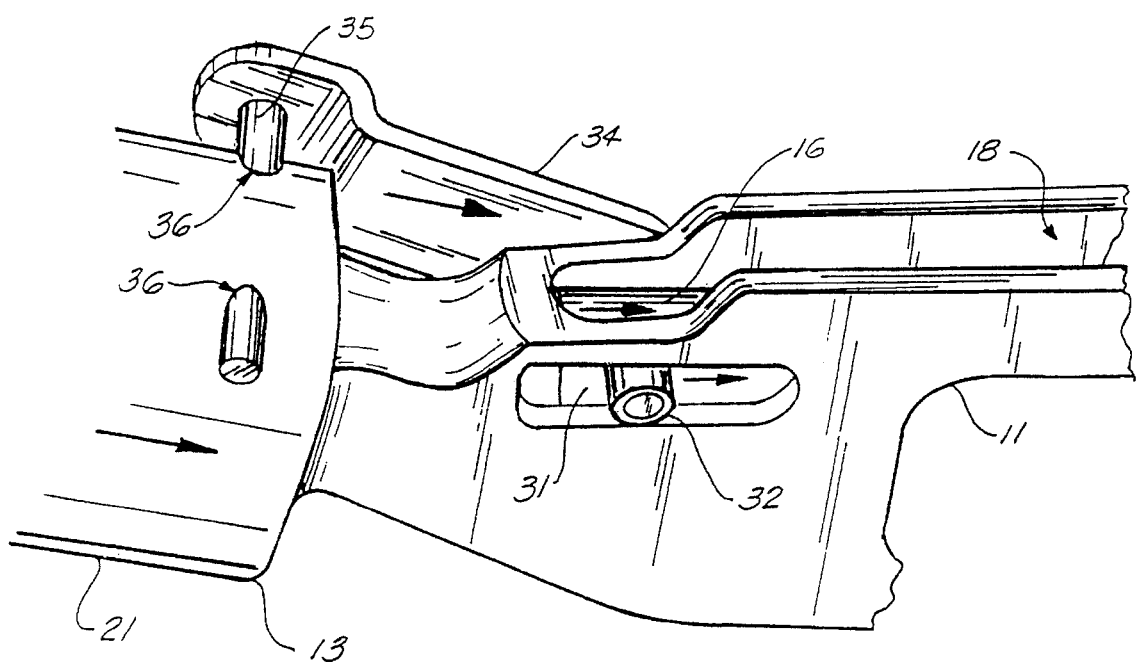
FIG. 10 is a partial perspective view of the preferred embodiment of the apparatus of the present invention.

Cylindrically shaped member 24 attaches to handle body 11 at narrowed portion 30. A pair of opposed slots 31,33 are placed on opposite sides of longitudinally extending slot 18. The slots 31,33 allow post 32 to extend through pushrod 16 and into each slot 31,33. The post 32 forms a connection with link 34 at one end portion of link 34. The opposing end portion of link 34 attaches to transverse post 35 (see FIG. 10). Post 35 is attached to cylindrical sleeve 21 at slot opening 36.

An angle 37 is formed between the central axis of socket 25 and the longitudinal axis of handle body 11 which is generally parallel to pushrod 16.

Figure 4:
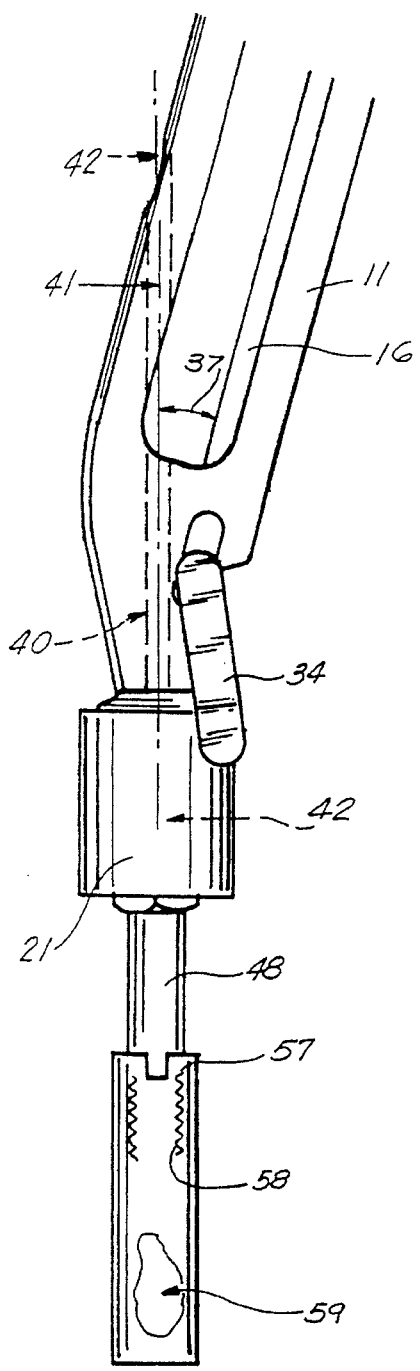
FIG. 4 is a fragmentary view of the first embodiment of the present invention.
Figure 5:
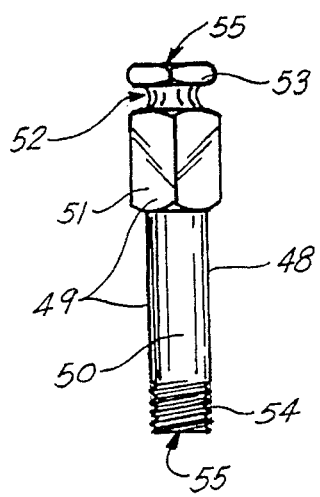
FIG. 5 is a partial view of the first embodiment of the present invention illustrating the nail puller portion thereof.

Cylindrical bore 39 is separated from the socket portion 25 by annular shoulder 38. Cylindrical bore 39 communicates with a smaller diameter passageways or channels 40,41 each having a common central axis 42. The channels 40,41 allow a wire to be placed through each channel 40,41 and into cylindrical bore 39 and then into socket 25. The wire can also be inserted into the intramedullary rod via the central bore 55 of nail puller 48. Axis 42 in FIG. 4 shows the central axis of channels 40,41. Angle 37 defines the angle between axis 42 and the central longitudinal axis of handle body 11 designated as 43 in FIG. 4.

A pair of opposed longitudinally extending slots 44,45 are positioned on opposite sides of cylindrical member 24. Pins 46,47 are provided on cylindrical sleeve 21, each of the pins 46,47 extending respectively into a slot 44,45. The pins 46,47 communicate with the end portions of the respective slots 44,45 to define limits of movement of cylindrical sleeve 21 relative to cylindrical member 24. Because of the connection between cylindrical sleeve 21 and pushrod 16 via link 34, this also defines the limits of travel of pushrod 16 and trigger 15.

Nail puller 48 includes an elongated shank 49 that includes a cylindrical head 50 and a hexagonal section 53. An annular groove 52 is positioned at one end portion of shank 49 adjacent hexagonal section 53. The opposite end of shank 49 provides a threaded end portion 54. Nail puller element 48 includes a longitudinal cylindrical bore 55 that extends the full length of shank 49.

Nail puller element 48 can threadably attach at threads 54 to intramedullary rod 56. The proximal end 57 of intramedullary rod 56 is provided with internal threads 58 that can engage the distal end 58 of nail puller element 48 at threaded portion 54. Intramedullary rod 56 is a commercially available surgical prosthetic device. Such a rod can be seen in the prior Brumfield patent 5,167,633 incorporated herein by reference. Intramedullary rods 56 typically include a longitudinal bore 59, a pair of diagonal openings 60,61, a pair of transverse openings 62,63. A plurality of bone screws (not shown) can be affixed through one of the openings 60–63 for affixing the intramedullary rod 56 to a patient's bone tissue. Bore 59 can extend the full length of rod 56. The distal end 58 can be a closed end.

In order to remove an intramedullary rod 56 from a patient's intramedullary canal (such as a femur) 68 the surgeon first threads nail puller 48 into the proximal end 57 of intramedullary rod 56. The surgeon can apply torque to the nail puller element 48 at hexagonal head 53 portion or to hexagonal section 51 using a wrench or like instrument.

Figure 7:
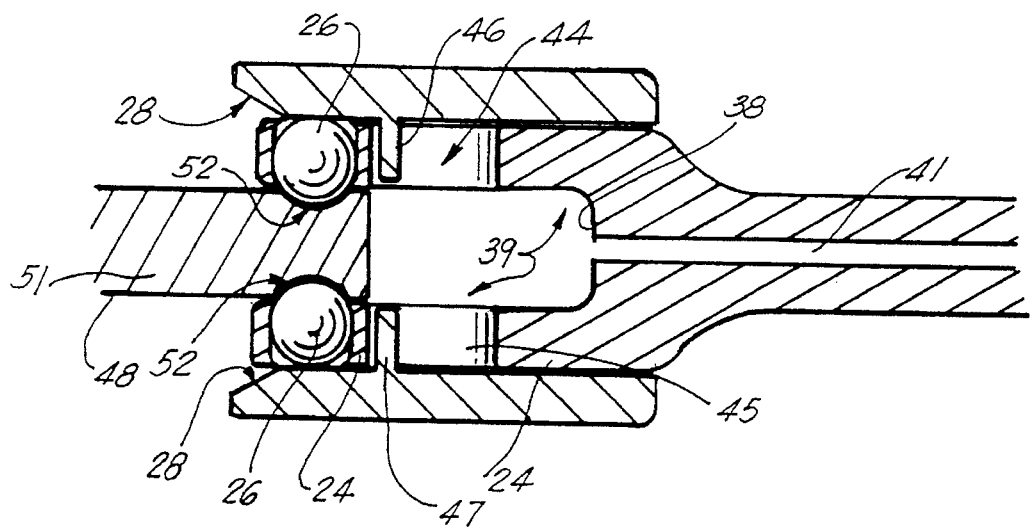
FIG. 7 is a fragmentary view of the first embodiment of the apparatus of the present invention in locking position.
Figure 8:
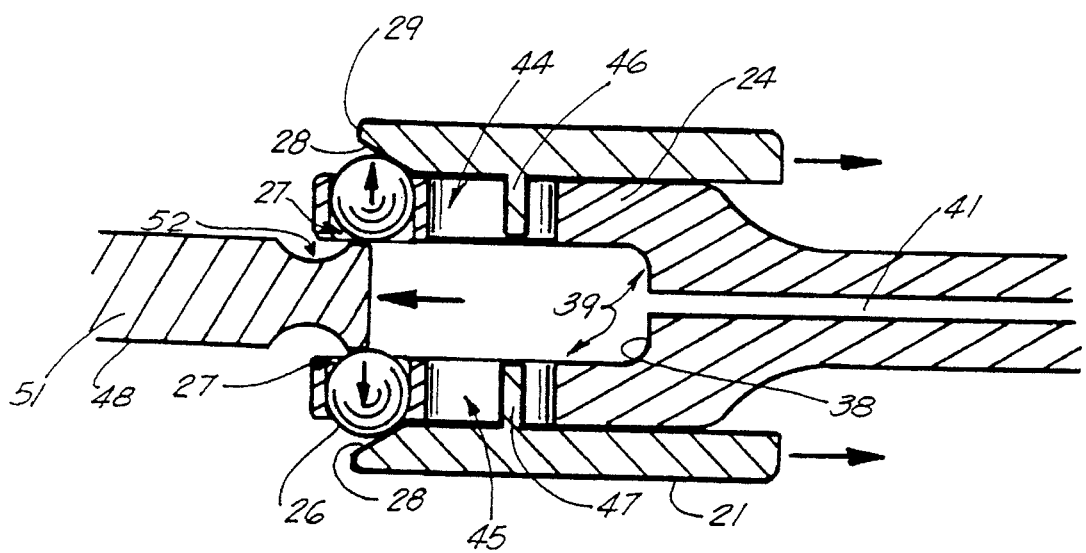
FIG. 8 is a fragmentary view of the first embodiment of the apparatus of the present invention releasing position.
Figure 9:
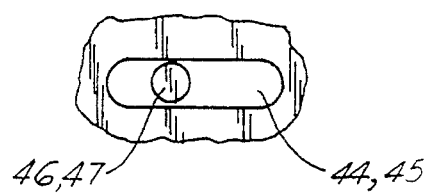
FIG. 9 is a fragmentary view of the preferred embodiment of the apparatus of the present invention.
Figure 11:
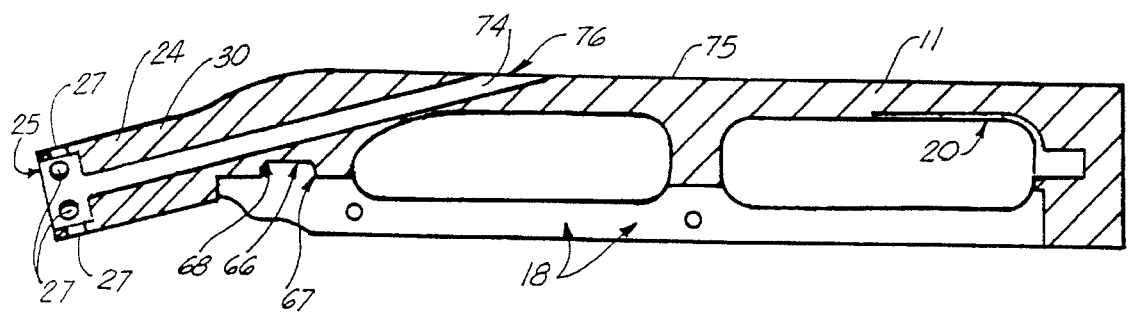
FIG. 11 is a side fragmentary view of a second embodiment of the apparatus of the present invention illustrating the handle body portion thereof.
Figure 12:
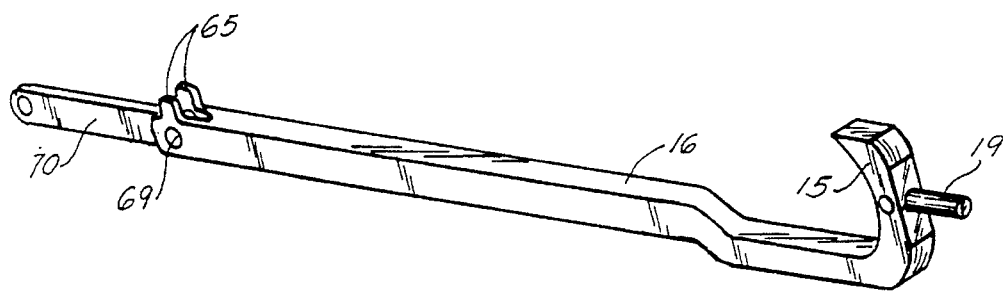
FIG. 12 is a fragmentary perspective view of the second embodiment of the apparatus of the present invention.
Figure 13:
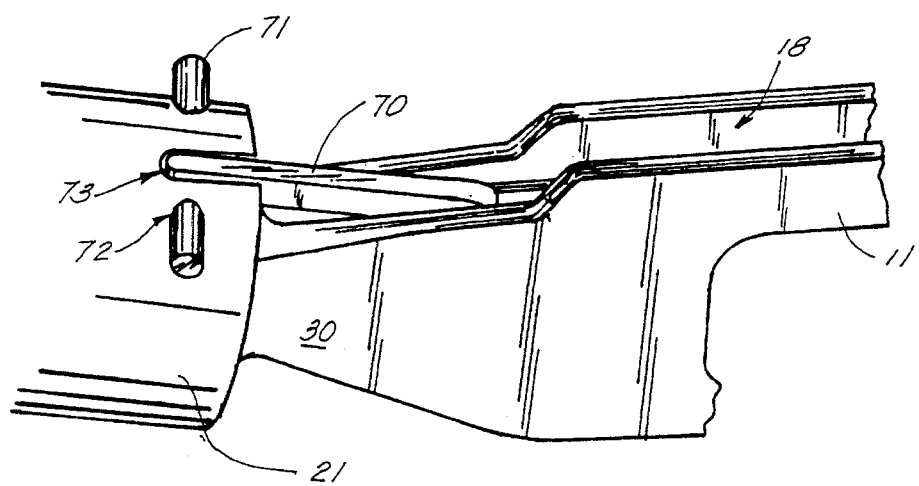
FIG. 13 is a partial perspective view of the second embodiment of the apparatus of the present invention.
Figure 14:
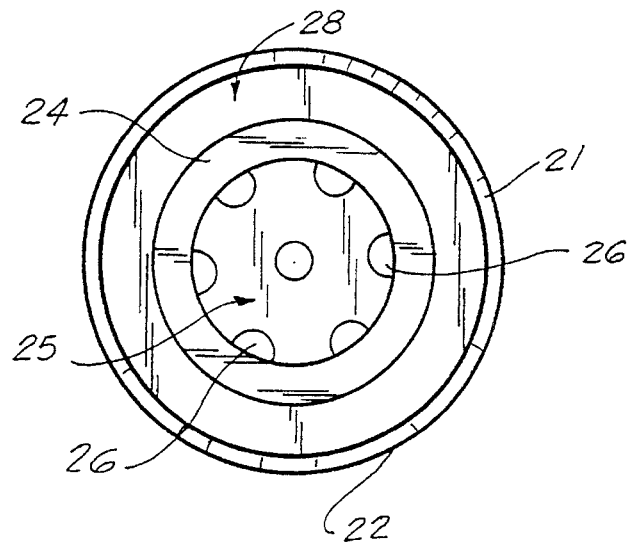
FIG. 14 is a fragmentary view of the second embodiment of the apparatus of the present invention.

The surgeon then pulls trigger 15 which retracts pushrod 68 and pulls link 34 and sleeve 21. This places the plurality of locking balls 26 adjacent beveled annular section 28 of sleeve 21. In the position, each of the locking balls 26 is free to travel toward the beveled annular surface 28 and away from hexagonal socket 25. This allows the nail puller element 48 to be withdrawn socket 25 as the locking balls 26 are released from the annular groove 52 of nail puller element 48. To insert a rod 56, the surgeon attaches nail puller element 48 to intramedullary rod 56 at proximal end 57 by threading the threaded end portion 54 into corresponding internal threads with bore 59. The surgeon then attaches handle 11 to the nail puller element 48 at head 51A, 53. The locking balls 26 register in annular groove 52. The surgeon releases the trigger to lock the balls 26 in locking position (FIG. 7). The surgeon can them impact the handle 11 to transmit force necessary to implant rod 56 into the patient's intramedullary canal. In FIGS. 11–13, a second embodiment of the apparatus of the present invention is shown illustrating a second construction of the linkage that includes the handle 11, pushrod 16, cylindrical member 24, and cylindrical sleeve 21. In FIGS. 11–13, the pushrod 16 provides a pair of tab 65 that extend transversely with respect to the central longitudinal axis of the pushrod 16. The tab 65 register with an elongated longitudinal slot 66. The pushrod moves between locking and releasing positions as with the first embodiment, but in the second embodiment, the locking tabs register with opposite end portions of the slot 66 depending upon whether the pushrod is in locking or releasing position. When a surgeon pulls the trigger 15 the locking tabs 65 register with end portion 67 of slot 66. When the surgeon releases the trigger 15, coil spring 17 urges the pushrod toward distal end 13 of handle body 11 and the tab 65 engage end portion 68 of longitudinal recess 66. A link 70 is pinned at pinned connection 69 to pushrod 16. Link 70 attaches to cylindrical sleeve 21 at pinned connection 71. Transverse pin 71 extends through transverse 72 and sleeve 21. One end portion of link 70 register in slot 73 of cylindrical sleeve 21 as shown in FIG. 13.

The cylindrical portion 24 is integrally formed with handle body 11 as shown in FIG. 11. Socket 25 is generally cylindrically shaped and carries the plurality of locking balls 26 at openings 27. A single diagonally extending channel 74 extends between socket 25 and the upper surface 75 of handle 11 at opening 76.

The following table lists the part numbers and part descriptions as used herein and in the drawings attached hereto.

PARTS LIST

| Part Number | Description |
| --- | --- |
| 10 | medullary nail remover |
| 11 | handle body |
| 12 | proximal end |
| 13 | distal end |
| 14 | anvil |
| 15 | trigger |
| 16 | pushrod |
| 17 | spring |
| 18 | longitudinal slot |
| 19 | post |
| 20 | groove |
| 21 | cylindrical sleeve |
| 22 | outer surface |
| 23 | inner surface |
| 24 | cylindrical member |
| 25 | socket |
| 26 | locking ball |
| 27 | opening |
| 28 | beveled annular surface |
| 29 | annular end portion |
| 30 | narrowed portion |
| 31 | slot |
| 32 | post |
| 33 | slot |
| 34 | link |
| 35 | post |
| 36 | transverse opening |
| 37 | angle |
| 38 | annular shoulder |
| 39 | cylindrical bore |
| 40 | channel |
| 41 | channel |
| 42 | axis |
| 43 | angle |
| 44 | slot |
| 45 | slot |
| 46 | pin |
| 47 | pin |
| 48 | nail puller element |
| 49 | shank |
| 50 | cylindrical section |
| 51 | hexagonal head section |
| 51A | cylindrical section |
| 52 | annular groove |
| 53 | hexagonal head section |
| 54 | threaded portion |
| 55 | cylindrical bore |
| 56 | intramedullary rod |
| 57 | proximal end |
| 58 | distal end |
| 59 | longitudinal bore |
| 60 | diagonal opening |
| 61 | diagonal opening |
| 62 | transverse opening |
| 63 | transverse opening |
| 64 | distal end |
| 65 | tab |
| 66 | slot |
| 67 | end of slot |
| 68 | end of slot |
| 69 | pinned connection |
| 70 | link |
| 71 | pin |
| 72 | transverse opening |
| 73 | slot |
| 74 | channel |
| 75 | upper surface |
| 76 | opening |

Because many varying and different embodiments may be made with in the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A combination intramedullary nail and insertion and removal apparatus for inserting and pulling the intramedullary nail having a longitudinal bore from a patient's intramedullary canal, comprising:

a) a handle body having proximal and distal end portions;

b) the handle body supporting a trigger that is movably disposed relative to the handle between locking and releasing positions;

c) the proximal end of the handle body having a socket with a central axis;

d) an intramedullary nail having proximal and distal end portions and a hollow bore;

e) a separate nail puller element having spaced apart proximal and distal end portions, each of said proximal and distal end portions having a connector that enables a connection to be formed respectively with the handle body distal end and the intramedullary nail proximal end portion; and f) the distal end of the handle body having means for forming a releasable connection with the nail puller at the socket when the trigger is moved between releasing and locking positions by a user.

2. The apparatus of claim 1 wherein the nail puller element is a tubular member with a bore.

3. The apparatus of claim 1 further comprising an anvil mounted at the distal end of the handle body.

4. The handle apparatus of claim 1 wherein the handle body has a longitudinally extending slot, and the trigger is movably mounted in the slot.

5. The handle apparatus of claim 4 wherein the handle body has a longitudinal axis, and the trigger includes an elongated rod that has a longitudinal axis that is generally parallel to the axis of the handle body.

6. The handle apparatus of claim 2 wherein the second tubular member is rigidly attached to the distal end of the handle body.

7. The handle apparatus of claim 6 wherein the socket is in the second tubular member, and the socket has a shaped portion that receives a correspondingly shaped head portion of the nail puller at the proximal end of the nail puller.

8. The handle apparatus of claim 7 wherein the socket of the second tubular member includes a larger diameter socket portion and a smaller diameter socket portion.

9. The handle apparatus of claim 8 wherein the handle body has a passageway with an axis that is coaxial with the axis of the socket.

10. The handle apparatus of claim 9 wherein the passageway forms an acute angle with the longitudinal axis of the handle body.

11. A combination quick release handle apparatus and intramedullary nail for pulling the intramedullary nail with a longitudinal bore from a patient's intramedullary canal, comprising:

a) a handle body having proximal and distal end portions;

b) the handle body supporting a pushrod that is movably disposed relative to the handle between locking and releasing positions;

c) the proximal end of the handle body having a socket with a central axis;

d) an intramedullary nail having proximal and distal end portions and a hollow bore;

e) a nail puller element having a distal end portion with means for forming a connection with the intramedullary nail at the proximate end of the nail at the nail longitudinal bore;

f) the nail puller element having a proximal end portion with an annular portion; and g) the distal end of the handle body having means, comprising at least in part a plurality of circumferentially spaced locking elements, for forming a releasable connection with the annular portion of the nail puller at the socket when the pushrod is moved between releasing and locking positions by a user.

12. The apparatus of claim 11 wherein the releasable connection means includes a first tubular member with a bore and a second tubular member disposed within the bore of the first tubular member.

13. The apparatus of claim 11 further comprising a trigger mounted to the pushrod at the distal end of the handle body.

14. The handle apparatus of claim 11 wherein the handle body has a longitudinally extending slot, and the pushrod is movably mounted in the slot, extending substantially the length of the handle body.

15. The handle apparatus of claim 14 wherein the handle body has a longitudinal axis, and the pushrod includes an elongated rod that has a longitudinal axis that is generally parallel to the axis of the handle body.

16. The handle apparatus of claim 12 wherein the second tubular member is rigidly attached to the distal end of the handle body.

17. The handle apparatus of claim 16 wherein the socket is in the second tubular member, and the socket has a shaped portion that receives a correspondingly shaped head portion of the nail puller at the proximal end of the nail puller.

18. The handle apparatus of claim 17 wherein the socket of the second tubular member includes a larger diameter socket portion and a smaller diameter socket portion.

19. The handle apparatus of claim 18 wherein the handle body has a passageway with an axis that is coaxial with the axis of the socket.

20. The handle apparatus of claim 19 wherein the passageway forms an acute angle with the longitudinal axis of the handle body.

21. The handle apparatus of claim 11 wherein the nail puller element has an enlarged head with an annular groove and the releasable connection forming means attaches to the head at the groove.

22. The handle apparatus of claim 21 wherein the enlarged head is hexagonally shaped in transverse section.

23. The apparatus of claim 10 wherein the nail puller element has a longitudinal bore 24. The apparatus of claim 11 wherein the nail puller element has a threaded portion thereon for forming a connection with the intramedullary nail.

25. The apparatus of claim 11 wherein the annular portion includes an annular groove and the releasable connection forming means comprises in part locking elements that nest in the annular groove.

\* \* \* \* \*